(12) United States Patent
Prat (10) Patent No.: US 7,556,804 B2
(45) Date of Patent: Jul. 7, 2009

(54) ANTI-HGF-R ANTIBODIES AND THEIR USE (75) Inventor: Maria Giovanna Prat, Turin (IT)

(73) Assignee: Universita degli Studi del Piemonte Orientale "Amedeo Avogadro", Vercelli (IT)

(*) Notice: Subject to any disclaimer, the term of this patent is extended or adjusted under 35 U.S.C. 154(b) by 437 days.

(21) Appl. No.: 10/559,305

(22) PCT Filed: Jun. 1, 2004

(86) PCT No.: PCT/EP2004/050976

§ 371 (c)(1),
(2), (4) Date: Dec. 2, 2005

(87) PCT Pub. No.: WO2004/108766

PCT Pub. Date: Dec. 16, 2004

(65) Prior Publication Data

US 2006/0140940 A1 Jun. 29, 2006

(30) Foreign Application Priority Data

Jun. 5, 2003 (IT) .................... MI2003A1127

(51) Int. Cl.
*A61K 39/395* (2006.01)
*C12P 21/08* (2006.01)
*C12P 21/04* (2006.01)
*C12N 5/06* (2006.01)

(52) U.S. Cl. ............ 424/143.1; 424/141.1; 530/388.1; 530/388.22; 530/809; 435/70.21; 435/326; 435/810

(58) Field of Classification Search ............ None
See application file for complete search history.

(56) References Cited

U.S. PATENT DOCUMENTS 5,686,292 A * 11/1997 Schwall et al. ........... 424/143.1

FOREIGN PATENT DOCUMENTS

| WO | WO 92/20792 | 11/1992 |
| WO | WO 98/00543 | 1/1998 |

OTHER PUBLICATIONS

Goodman and Gilman, 10th edition, McGraw-Hill, 2001, p. 3-29.*
Prat, et al., "Agonistic Monoclonal Antibodies Against the Met Receptor Dissect the Biological Responses to HGF," Journal of Cell Science, vol. 111, No. Part 2, pp. 237-247 (1998).
Ohashi, et al., "Sustained survival of human hepatocytes in mice: A model for in vivo infection with human hepatitis B and hepatitis delta viruses," Nature Medicine, vol. 6, No. 3, pp. 327-331 (2000).

* cited by examiner

*Primary Examiner*—Manjunath N Rao
*Assistant Examiner*—Shulamith H Shafer
(74) *Attorney, Agent, or Firm*—Heslin Rothenberg Farley & Mesiti P.C.

(57) ABSTRACT

The present invention relates to monoclonal antibodies which recognize the chain of the HFG receptor with the agonist activity of the natural ligand. The invention also relates to the hybridoma which secretes said antibodies and to their therapeutic and diagnostic use.

10 Claims, 10 Drawing Sheets

ANTI-HGF-R ANTIBODIES AND THEIR USE

CROSS REFERENCE TO RELATED APPLICATIONS

This application is a 371 filing of PCT International application no. PCT/EP2004/050976 filed Jun. 1, 2004 and published in English as WO 2004/108766 on Dec. 16, 2004 which claims the priority of Italian Application No. MI2003A001127 on Jun. 5, 2003, the disclosures of which are hereby incorporated by reference in their entirety.

FIELD OF THE INVENTION

The technical field of the invention is represented by molecules of diagnostic and therapeutic interest having molecular specificity for the hepatocyte growth factor receptor (HGF-R).

PRIOR ART

HGF (Hepatocyte Growth Factor) and its receptor (HGF-R also known as Met, on the basis of the proto-oncogene encoding it) are a functional pair from which many different biological activities depend. Following interaction with its receptor, HGF stimulates proliferation not only of hepatocytes, but also of other epithelial cells, endothelial cells, melanocytes, hemopoietic cells and bone cells. HGF is also a survival factor, promotes the dissociation of epithelial cells (scatter effect) and cell motility, stimulates invasive growth and cell polarisation, necessary events for tubular morphogenesis and ramification of tubular structures.

In addition, activities of the HGF/HGF-R system have been detected in vivo on the neural system, kidney and mammary glands; HGF also has a role in embryo development, angiogenesis and tissue regeneration. During embryogenesis, HGF is essential for the development of the liver and the placenta and for migration of myoblast precursors to the limb buds (see review by Trusolino and Comoglio, Nat Rev Cancer, 2:289-300, 2000).

This ligand-receptor pair is also implicated in pathological phenomena, such as the formation of tumours and metastases (see review by Comoglio and Trusolino, J Clin Inv., 109:857-862, 2002). HGF-R is a heterodimeric tyrosine kinase of 190 kD, consisting of an α chain and a β chain of 50 kD and 145 kD respectively, joined by a disulfide bridge. The α chain is extracellular whereas the β chain is transmembrane and contains three domains: an extracellular one which binds HGF, an intracellular one which contains the kinase domain and the transmembrane one which unites them. The mature heterodimeric form of this receptor derives from a 170 kD single chain precursor by proteolytic cleavage. Two truncated isoforms of HGF-R, also heterodimeric, have been identified of 140 kD (p140) and 130 kD (p130) respectively. They are derived from the internal receptor by proteolytic cleavage at the C-terminal portion of the β chain. They both lack the kinase domain: in particular protein p140 is anchored to the plasma membrane via the transmembrane segment, while protein p130 lacks this segment and is therefore soluble in biological fluids or in the supernatant of cell Anti-HGF-R antibodies have until now been used for diagnostic purposes, to verify receptor distribution in normal and neoplastic tissues (Prat et al., Int. J. Cancer, 1991, 49:323-328; Di Renzo et al., Oncogene, 1992, 6:1997-2003.) HGF-R is implicated in tumorigenesis with various mechanisms: it can be overexpressed, amplified, ectopically expressed, or can be activated following point mutations (see review by Comoglio and Trusolino 2002). Anti-HGF-R antibodies specific for extracellular and intracellular domain of the receptor β chain are described in Prat et al., Mol. Cell. Biol., 1991, 11:5954-62 (also WO 92/20792). Monoclonal antibodies specific for the cytoplasmic domain of the human c-Met receptor have also been described in Bottaro et al., Science, 1991, 251:802-804.

Anti-c-Met monoclonal antibodies have also been used for dissecting the various biological activities of the receptor or exploiting the therapeutic potential thereof: for example in Prat M. et al., J. Cell. Sci., 1998, 111:237-247 anti-HGF-R antibodies have been studied and characterised as partial or full agonists, capable of partially or fully activating the range of responses induced by HGF; in WO 98/00543, antibodies with the agonist activity of HGF for the therapy of liver pathologies are described.

SUMMARY OF THE INVENTION

The present invention relates to monoclonal antibodies having specificity for the Hepatocyte Growth Factor receptor (HGF-R) and directed against the same epitope recognised by the antibody produced by the ICLC N. 03001 hybridoma deposited at the CBA in Genoa.

Said antibody recognises the extracellular domain of the HGF receptor β chain and recognises with equal efficiency the same epitope on the HGF-R of mice, rats, dogs, pigs and man.

Further aspects of the invention are represented by the antibody in a substantially purified form, by the hybridoma, by the diagnostic use of the antibodies produced, as well as by diagnostic kits comprising the antibodies described.

According to a further aspect, the invention comprises the therapeutic use of antibodies in the preparation of drugs with cardio- and hepato-protective activity.

DESCRIPTION OF THE FIGURES

The patent or application file contains at least one drawing executed in color. Copies of this patent or application publication with color drawing(s) will be provided by the Office upon request and payment of the necessary fee.

The supernatant of the NO-23 antibody secreting hybridoma (lane a) was assayed by Western-blotting with the HGF receptor purified by immunoprecipitation with an antibody that recognizes the receptor β chain (DO-24, Upstate Biotechnology Incorporated, Salt Lake City, USA) and separated by electrophoresis on SDS-PAGE under reducing and non reducing conditions. Under non reducing conditions the 190 kD heterodimeric form (lane a) is observed, while under reducing conditions, the NO-23 antibody recognizes only the β chain of the 145 kD HGF-R and the 170 kD precursor (Pr170) (lane b).

GTL-cells were grown in culture medium, washed and incubated with the NO-23 antibody at 4° C. in the presence of NaN$_3$ for 30 minutes. The binding of the NO-23 antibody on the cell membrane was displayed by means of anti-mouse Ig rabbit antibodies labelled with fluorescein, which were incubated at 4° C. for 30 minutes.

GTL-16 cells were labelled in vivo with [$^{35}$S] methionine and treated or not treated with tunicamycin, a substance which inhibits N-glycosylation. The cell extracts were then prepared, immunoprecipitated with the NO-23 antibody and loaded onto SDS-PAGE under reducing conditions. The epitope recognized by the antibody of the invention is present both on the β chain of the glycosylated receptor of cells not treated with tunicamycin (lane a) and on a protein extracted from treated cells (lane b) indicating that said epitope is proteic in nature. In this case the non glycosylated precursor of the receptor has an apparent molecular weight of 150 kD. In the case of untreated cells the 170 kD glycosylated precursor is also visible.

The double determinant radioimmunometric assay was undertaken as follows: the HGF-R antibody DL-21 (Upstate Biotechnology) was made to adhere to polyvinyl chloride microplates and was used to capture the soluble p130 isoform of the receptor. The assay indicated displacement of the $^{125}$I (radiolabelled marker) labelled HGF, on the receptor attached to the plate (shown on the Y-axis as percentage binding inhibition of the radiolabelled ligand x100), by: unlabelled HGF (-•-), antibody of the invention NO-23 (-■-) or Epidermal Growth Factor (—○—) (ligand not correlated). The NO-23 antibody does not compete with HGF for binding with HGF-R.

The double determinant assay was undertaken as described in FIG. 4. In panel A the DL-21 antibody was used to capture the soluble form of the receptor. The assay indicates displacement of the antibody NO-23 of the invention labelled with $^{125}$I (used as a radiolabelled marker), on the receptor attached to the plate (shown on the Y-axis as percentage binding inhibition of the radiolabelled antibody x100), by the unlabelled NO-23 antibody (-■-), by commercially available antibodies for HGF-R such as DO-24 (- -) (Upstate Biotechnology Inc.) and by DN-30 (-▲-). In panel B, antibody DO-24 was instead used for capturing HGF-R and antibody NO-23 labelled with $^{125}$I as tracer was used for displacement with the same unlabelled NO-23 (-■-), the DN-30 antibody (- -) and the DL-21 antibody (-▲-). None of the antibodies used, apart from antibody NO-23, was able to compete with the radiolabelled NO-23 antibody on the HGF-R, indicating that the site recognized by the various antibodies is different.

FIG. 6. Mapping of the epitope recognized by the antibody NO-23 on the HGF-R of species different from man, by kinase assay Cell extracts of H9c2 rat cells (lane a), mouse MLP-29 (lane b) and dog MDCK (lane d) were immunoprecipitated with the antibody of the invention NO-23; the precipitates were incubated for a kinase activity assay with 10 μCi [γ-$^{32}$P] ATP (specific activity: 7000 Ci/mM; Amersham) for 15 min at 30° C., washed and then separated on SDS-PAGE under reducing conditions (R, right) and non-reducing conditions (NR, left). The same experiment was conducted with GTL-16 human cell extracts (lane c) for control.

The assay was conducted by producing a wound in the monolayer of KS-IMM cells by means of a plastic tip and verifying the effects of the incubation in the presence and absence of HGF or of the antibody of the invention (see example 4). Panel A: untreated KS-IMM cells; panel B: KS-IMM cells treated with HGF; panel C: KS-IMM cells treated with the antibody of the invention NO-23.

Rat cardiomyocytes (cell line H9c2) were pretreated for 1 hour with the monoclonal antibody (NO-23) of the invention, with an anti-HGF-R reference antibody (DO-24), with a non-correlated antibody (AR-3), with HGF (0.3 nM), or left untreated (none), before inducing apoptosis by treatment with the cytotoxic agent daunomycin (10 μM) for 24 hours. The antibodies were used in a final concentration of 20 nM. Cell survival was evaluated with the colorimetric MTT assay, based on the formation of formazan salts, which are produced only from metabolically active cells, but not from apoptosis or necrosis induced cells. The value was expressed in percentage (%) as (absorbance in each well)/(absorbance in control wells not treated with daunomycin)×100.

Primary rat hepatocytes were pretreated for 15 min with 25 nM (-◇-), 50 nM (-x-) of the monoclonal antibody NO-23 or with a non-correlated control antibody AR-3 (50 nM, -▲-), before inducing apoptosis by hypoxia treatment with a stream of 95% $N_2/CO_2$ as described in example 5. Controls: hepatocytes not treated with the antibody (-■-); hepatocytes not treated by induction of hypoxia (-●-).

The antibody NO-23 shows a protective effect on the primary rat hepatocytes where apoptosis had been induced: in this respect, FIG. 9 shows that at one and a half hours from treatment under hypoxia conditions, the hepatocytes pretreated with the antibody NO-23 have a survival greater than 50%. The cell survival was measured by counting the viable cells after staining the non viable hepatocytes with Trypan Blue.

H9c2 rat cardiomyocytes were stimulated with increasing concentrations of antibody NO-23 for 12 minutes at 37° C. (10, 50, 250 nM NO-23), corresponding to lanes b, c, d) or were left untreated (lane a). Cell extracts were then immunoprecipitated with an anti-HGF-R antibody, separated electrophoretically and transferred onto nitrocellulose. Phosphorylation of the receptor was detected with anti-phosphotyrosine antibodies and then with an anti-mouse immunoglobulin secondary antibody.

DETAILED DESCRIPTION OF THE INVENTION

Definitions

The terms "HGF receptor" (HGF-R) and "c-Met" are used to define the cell receptor for Hepatocyte Growth Factor. HGF is a 190 kD heterodimeric protein, comprising an extracellular α chain and a β chain, joined by a disulfide bridge. In the β chain, transmembranous, the cytoplasmic domain possesses kinase activity. Two forms truncated at the C-terminal of the HGF-R β chain are also known, being a heterodimeric of 130 kD (soluble) and of 140 kD respectively, both lacking the kinase domain. For the purposes of the present invention, the term HGF-R includes all known variants or fragments thereof which retain the ability to bind HGF.

The term "antibody" comprises the intact immunoglobulin molecule, as well as its functional fragments, such as Fab, F(ab')2, or Fv which maintain the properties of the antibody intact. Particularly preferred are the bivalent antibody fragments or F(ab')2.

In particular the variable regions of the light and heavy chains are able to bind the antigen, in accordance with the structural characterisation given by Chothia et al., J. Mol.

Biol., 186:651-663 (1985) and by Novotny & Haber, Proc. Natl. Acad. Sci. USA, 82:4592-4596 (1985), said ability being related to the variability of the amino acid sequence concentrated in three regions, namely CDR (Complementarity Determining Region) as defined in Kabat, E. A. et al., Sequences of Proteins of Immunological Interest, National Institutes of Health, Bethesda, Md. (1987).

The constant domains of the antibody are not directly involved in binding with the antigen but are responsible for the effector activities of the antibody, such as (i.e.) for the Antibody Dependent Cellular Cytotoxicity (ADCC).

The term "monoclonal antibody" comprises all antibodies derived from a single cell clone or hybridoma derived from the fusion of myeloma cells and spleen cells of immunized rodents, in accordance with the technique of Milstein C. From this the corresponding chimeric antibodies can be derived by means of techniques known to the expert of the art.

The term "epitope" refers to a determined group of atoms or amino acids which are recognized in a specific manner (with an affinity constant greater than $10^{-5}$ M) by a different molecule. In the present invention, an epitope recognized by an anti-HGF-R antibody refers to the group of amino acids, having part of the amino acid sequence of HGF-R, able to bind the antibody of the invention. The epitope can be linear or discontinuous.

The terms "treatment" and "therapy" comprise curative, prophylactic and preventative therapies.

DESCRIPTION

The present invention relates to monoclonal antibodies which recognize an epitope positioned on the extracellular domain of the HGF receptor β chain. This epitope is different from both that recognized by the natural ligand, HGF, and from other characterised and commercially available antibodies, such as for example the antibodies DO-24, DL-21 (Upstate Biotechnology), as is easily determinable by an expert of the art by means of competition assays or double determination immunoassays, such as for example those described in Prat et al. J. Cell Sci., 1998, 111: 237-247. The antibodies of the invention are preferably murine. They are also preferably bivalent, preferably in the Fab(2) form or native form, composed of two heavy chains and two light chains, comprising the constant region or Fc. These antibodies can be labelled with fluorescent groups, or with enzyme tracers, such as alkaline phosphatases or peroxidases, or with biotin for detection by means of avidin or streptavidin, or also with radioactive groups or atoms, such as for example $^{125}$I, $^{35}$S, $^{14}$C, $^{3}$H.

The epitope recognized by the antibodies of the invention is expressed in vivo on cultured GTL-16 cells, and is thus a native epitope. Moreover, it is also recognized with equal efficiency after denaturation of the HGF-R following treatment with ionic detergent SDS and heated for a short time (95° C. for 5 minutes) as required for example by the SDS-PAGE technique. The HGF-R epitope recognized by the antibodies of the invention is therefore resistant to denaturation induced by ionic and non-ionic detergents and that induced by thermal treatment at temperatures above 70° C. Furthermore, the epitope is resistant to the action of reducing agents such as β-mercaptoethanol and hence, presumably, does not contain disulphide bridges and is linear in nature.

The binding between the HGF-R epitope and the monoclonal antibodies of the invention is a high affinity binding with a constant greater than $10^{-7}$ M, preferably $10^{-8}$ M; furthermore, said binding is resistant to treatment with non-ionic detergents, such as for example Triton, preferably Triton X-100 and NP-40.

The epitope recognized by the antibodies of the invention has an amino acid sequence which is immunologically indistinguishable on the HGF receptor of animal species different from man, for example mice, dogs, rats and pigs. Said receptors are recognized with similar efficiency to human HGF-R, as can be determined by immunoprecipitation in solid or liquid phase. The antibody of the invention can therefore by used for detecting the HGF-R of various mammalian species other than man, such as rodents, (mice and rats), canids (dogs) and ruminants (pigs).

It is particularly useful for providing animal models for the study of biological effects activated by the HGF/HGF-R system. Therefore in one of its preferred aspects, the invention relates to the use of antibodies of the invention for evaluating agonistic effects of the HGF receptor in animal experimental systems. In one of its preferred embodiments, the antibody is identified by the symbol NO-23, having isotype γ2a/κ, and is produced by hybridoma number PD03001 deposited 12th Feb. 2003 at the Centro Biotecnologie Avanzate of Genoa. The hybridoma derived from the fusion of spleen cells from a BALB/c mouse immunized with GTL-16 cells (as described in Prat. M. et al. Mol. Cell. Biol. 1991, 5954-5962) with myeloma cells, preferably with P3×63.Ag8.653 cells, in accordance with known techniques (Kohler G, Milstein C. Nature, 256:495-497, 1975). The hybridoma grows in suspension preferably in RPMI-1640 medium containing serum or suitable growth factors, preferably FCS, in quantities comprising from 5 to 15%, preferably 10%. The medium preferably contains antibiotics such as penicillin and streptomycin and, optionally, fungizone and β-mercaptoethanol ($5 \times 10^{-5}$ M). The hybridoma is maintained in culture by diluting with fresh medium every two or three days, in ratios of between 1:2 and 1:4 (spent medium/fresh medium). The antibody of the invention is obtained by fermenting large quantities of hybridoma cells; the antibody is secreted into the hybridoma culture medium from which it can be purified in accordance with known chromatographic techniques. From the hybrodoma secreting the NO-23 antibody the encoding nucleotide sequence can be obtained by means of techniques known to the expert of the art, such as cloning of the cDNAs coding for the light chain and the heavy chain with suitable degenerate oligonucleotide primers, such as the universal ones described in Orlandi et al. Proc. Natl. Acad. Sci. USA 1989;86:3833-7.

A further aspect of the invention is represented by the hybridoma secreting the antibody and which can be used for the production of the antibody in ascites or for large scale production in bioreactors in accordance with methods known to the art, such as for example batch culturing, culturing in a bioreactor, for example a hollow fibre bioreactor, in accordance with techniques known to the expert of the field (Yang et al, Biotechnol Bioeng, 2000, 69:74-82). The antibodies of the invention are purified from the hybridoma supernatant or ascitic fluid by techniques known for immunoglobulin purification, such as precipitation in high concentrations of salts, preferably ammonium sulphate, followed by dialysis and gel filtration and, optionally, affinity chromatography.

Thus, according to a further aspect, the invention relates to the antibody produced from hybridoma number PD03001, deposited on 12th Feb. 2003 at the Centro Biotecnologie Avanzate in Genoa, preferably in a purified form.

The antibody of the invention is characterised by agonistic activity for the HGF receptor and, as with the natural ligand (HGF), induces phosphorylation of the HGF-R intracytoplasmic domain. The antibody of the invention can then stimulate the plethora of activities induced by the natural ligand. In contrast to the latter, it possesses a greater stability and can be produced, purified and suitable stored in large quantities.

The biological activity induced by the HGF/HGF-R binding by the antibody of the invention is measurable in vitro by means of assays known to the art. For example mitogenic activity induced by HGF-R activation is measurable by assays of the proliferation of cells derived from primary lines or cultures, preferably of cells derived from primary hepatocyte cultures (Naldini et al. EMBO J, 1991, 10:2867-78) or on cell lines derived from endothelium (Huvec cells). Biological activities induced by HGF or its agonists can also be measured by means of other assays such as tubulogenesis and angiogenesis as described in Prat et al., (J. Cell Sci., 1998, 111:237-247); motogenic activity is measurable by cell migration assays, for example by a wound healing assay or dissociation of epithelial cell colonies (scatter effect, Prat et al., J Cell Sci., 1998). Activation of the receptor is also measurable by evaluating phosphorylation of the receptor β chain cytoplasmic domain, for example with antibodies specific for phosphorylated tyrosine, or with antibodies specific for the phosphorylated form of the receptor or, in another direct manner, by evaluating incorporation of radiolabelled inorganic phosphate administered to the cells as $^{32}P$ ortho-phosphate.

The antibodies of the invention demonstrate in vitro biological activity typical of HGF-R agonists, as described in Prat M, et al., J Cell. Sci., 1998, 111:237-47, i.e. able to activate both motogenic activity and mitogenic activity normally induced by the natural ligand. This is a surprising characteristic of the antibody of the invention considering that the epitope recognized by the two ligands on the HGF-R is different, as determined by means of double determinant assays.

Furthermore, surprisingly, these antibodies possess an antiapoptotic activity on target cells, preferably represented by hepatocytes and cardiomyocytes. This activity is indicated in vitro for example by pre-treating primary hepatocytes or cell line H9c2 (rat cardiomyocytes) with the antibodies of the invention and inducing cell-specific proapoptotic stimuli, such as for example hypoxic stress on hepatocytes, for example with a $CO_2/N_2$ atmosphere or by treating cardiomyocytes with cytotoxic agents, such as for example daunomycin.

As showed in these assays that will be further detailed in the experimental part, cell survival achieved by pre-treating primary hepatocyte and cardiomyocyte cultures with the antibodies of the invention is greater than that obtained after treatment with HGF itself. Furthermore, the monoclonals of the invention possess a binding affinity of the same order of magnitude as that of the natural ligand (greater than $10^{-7}$ M, even more preferably greater than $10^{-8}$ M). Said affinity, on the antibodies of the invention, is coupled with a greater stability than the natural ligand.

According to a further aspect, the antibodies of the invention are used in the medical field for both a diagnostic and therapeutic purpose. It is known that anti-HGF-R antibodies are used to evaluate hyperexpression of the receptor which can lead to increased cell proliferation. The HGF receptor is particularly hyperexpressed in solid tumours, particularly in carcinomas of the liver and the gastro-intestinal tract, and is also expressed in carcinomas of the ovary. In carcinomas of the thyroid, pancreas, non-small cell lung (NSCLC) and kidney, HGF-R is expressed at detectable levels, in contrast with non-detectable levels in normal tissues.

The antibodies of the invention are hence used in diagnostic applications for pathological conditions where the HGF receptor is expressed differently from normal tissue, or where it is hyperexpressed, in the diagnosis of the aforelisted pathologies, by means of immunohistochemistry or immunoenzymatic assays.

The diagnostic immunoassays are effected on samples consisting of cell extracts, biopsy sections or isolated cells derived from biopsies. The antibodies of the invention are preferably used in ELISA assays, preferably double determinant, in combination with monoclonal antibodies which recognize a different epitope from that recognized by the antibodies of the present invention. Anti-HGF-R monoclonal antibodies are known and commercially available, such as antibodies supplied for example by Upstate Biotechnologies.

According to a further aspect of both diagnostic and therapeutic value, the antibodies of the invention are used for purifying carcinomatous cells from biopsy specimens, preferably by means of immunomagnetic techniques whereby the antibody of the invention, previously coupled to magnetic beads, is used to bind metastatic cells which express the HGF receptor differently from normal cells.

According to said application the antibody bound to magnetic supports enables carcinoma micrometastasis which express the HGF-R to be purged from bone marrow. The cells, selected and bound by way of the antibody to the magnetic beads, are in their turn easily separated from the tissue by using a magnet (Kielhorn et al., Cancer, 94:205-11, 2002).

The scope of the present invention also includes the antibodies which are bound co-valently or not to solid supports, such as synthetic surfaces of polypropylene, polyethylene, or spherical surfaces such as beads, preferably metallic and magnetic, of agarose or other materials compatible with the required application, and the surfaces comprising said antibodies.

The double determinant ELISA assays characterised by using the antibody of the invention are based on capturing the receptor, preferably the soluble form of the p130 HGF receptor. The antibodies of the invention are used in combination with other antibodies, preferably monoclonal or with the natural ligand, or can be used in combination with specific antibodies able to detect the phophorylated and hence active form of the receptor.

In this latter case, the receptor can be prepared for example from cell extracts of cells stimulated with HGF, optionally In the presence of molecules or collections of molecules (libraries) of which the determination of biological activity or agonistic/antagonist activity of the HGF-R is desired.

The receptor can also be prepared from extracts of tumour biopsy pieces in which the receptor is active, consequent to hyperexpression or ectopic expression, which can entail the activation thereof to begin an autocrine and/or paracrine circuit.

Should this latter be the case, as in the case of point mutations, the HGF receptor can be in an activated state, i.e. phosphorylated in tyrosine, although expressed at normal levels. Activating point mutations moreover have been found in papilliferous carcinomas of the kidney and young hepatocarcinomas. It is known that the tumorigenic potential of HGF-R is not only related to its level of expression but also to its activation level (i.e. phosphorylation).

According to a further aspect, the invention relates to the use of the antibodies of the invention in immunometric assays, preferably in a double determinant ELISA or radioimmunometric assay, in which the antibody of the invention is used to capture HGF-R in solid phase, possibly solubilized with a buffer containing phosphatase inhibitors preferably specific for tyrosine phosphorylation, in combination with a tracer antibody which recognizes specifically the phosphorylated form of the receptor. Such an assay therefore represents a diagnostic tool in cases where a pathological condition is determined by the activation of the receptor, caused by mutation rather than its hyperexpression, as in papilliferous carcinomas of the kidney and young hepatocarcinomas.

The epitope recognized by the antibodies of the invention is particularly stable: therefore the antibodies of the invention are particularly suitable for detecting the HGF receptor on fresh or fixed sections in immunohistochemical assays, preferably performed on cryostatic sections.

The antibodies of the invention are also particularly suitable for showing the presence of the receptor by means of other assays such as the Western-blot or immunoprecipitation in homogenous or heterogenous phase; the efficiency of recognition between the HGF-R and the antibodies of the invention are not reduced either by denaturation of the receptor, for example on SDS-PAGE, nor by the presence of detergents, preferably non-ionic which are used in general for the preparation of cellular extracts, in the immunoprecipitation mixture.

The biological activity peculiar to the antibodies of the invention manifests itself on target cells by a protective effect against apoptosis or programmed cell death, detectable in particular on cardiomyocytes and hepatocytes. Therefore the antibodies of the invention are used in the medical field not only for diagnostic purposes but also for therapeutic purposes for preparing medications to prevent and treat the effects of acute cellular stress which induce apoptotic damage as cellular response.

Use of the antibodies of the invention is particularly preferred for preparing medications for treating and preventing myocardial damage as a result of ischemia.

The antibodies of the invention are also particularly effective in treating and preventing acute damage of the myocardium derived from treating with chemotherapy agents which are often cardiotoxic, such as daunomycin, or viral infection of the myocardium.

A further preferred aspect of the invention is the use of the antibodies of the invention for preparing a pharmaceutical for treating and preventing hepatic damage due to various causes, such as apoptotic stress. In particular disclosed antibodies are useful for treating acute hepatic damage. Their activity is also apparent in vitro on cultured hepatocytes. The antibodies of the invention also find use in the prevention and treatment of damage to epithelial tissue, caused by necrosis or apoptosis, following, for example, traumatic events.

Apoptotic stresses are reproducible in vitro by means of hypoxia induced by a $CO_2/N_2$ atmosphere or administering compounds with cytotoxic and antiproliferation activity commonly used in the chemotherapy of tumours, such as daunomycin.

Cellular apoptosis can nevertheless be induced also by acute or chronic degenerative pathologies, such as trauma, inflammatory events of viral as well as ischemic etiology.

The compounds of the invention are preferably administered as compounds in combination with diluents or pharmaceutically acceptable excipients, preferably by parenteral means or by localized perfusion.

Their activity and their stability renders them particularly adapted for preparing solutions for conserving isolated organs. In accordance with this aspect the antibodies of the invention are preferably diluted with isotonic buffers, preferably with physiological solutions, in concentrations between 1 mg and 1 ng/ml, optionally in combination with other proteins or with the molecules or polymers most suitable for finally stabilizing in aqueous solution.

The antibodies of the invention can also be used for analytical purposes to verify the expression of HGF-R; they are particularly useful for the study of the biological activities of the HGF-R in in vitro cell systems as they mimic the natural ligand.

They are furthermore used for preparative purposes for the purification or dosage of the HGF-R receptor, for example after conjugation on matrices used for the preparation of chromatographic columns.

A further aspect of the invention regards diagnostic, analytical or preparative kits, and manufactured articles comprising one or more tubes containing the antibodies of the invention and suitable solutions for their use in a diluted form.

The diagnostic kits of the preferred embodiments contain, in addition to the antibodies of the invention:

reagents and diluents for using the antibody in immunometric assays preferably in ELISA type assays, or immunoprecipitation, or Western-blot;

reagents and buffers for preparing cell extracts from the tissue or cell culture from which measurement of the level of expression or the level of HGF-R activation is required, said buffers consisting preferably of physiological solution optionally comprising suitable detergents, preferably non-ionic, or other antibodies to be used for indirect detection of the antibodies of the invention;

filters, syringes or empty tubes that facilitate the use of the antibodies of the invention for diagnostic, therapeutic, analytical purposes or for the purpose of preparing the HGF-R as proposed in the description of the present invention;

fixing agents for the cryostatic tissues or sections where HGF-R is to be detected beads, preferably magnetic, ELISA microplates, nitrocellulose strips etc.

instruction leaflets relating to the methods used and the buffers to use for diluting the sample.

In a preferred aspect thereof, the kits of the invention comprise a tube containing the antibody of the invention and the anti-HGF-R-antibodies having different specificity therefrom, preferably having specificity for the phosphorylated form of the HGF-R such as for example the antibodies from the Biosource company, catalogue n. 44-882, 44-888, 44-892, 44-896.

Experimental Part

Example 1

Preparation of the Hybridoma

GTL-16 cells (derived from a human gastric carcinoma) characterised by amplification of the protooncogene Met and by its increased expression (Giordano et al. Mol. Cell. Biol., 1988, 8:3510-3517) were used as immunogen (Prat M. et al. J. Cell. Sci. 1998, 111:237-47). Immune spleen cells were fused with the P3×63.Ag8.653 myeloma line and subcloned by serial limiting dilutions.

The hybridoma supernatants containing the monoclonal antibodies were selected for their capacity to precipitate the HGF-R from cell extracts, by the following steps: incubation with GTL-16 cell extracts prepared in DIM buffer (see Prat et al., Mol. Cell. Biol., 1991, 5954-62) containing 1% Triton X-100, immunoprecipitation of the complexes by Protein A-Sepharose coated with goat anti-mouse Ig antibodies, further separation of the immunoprecipitates on SDS-PAGE, transfer onto nitrocellulose and comparison with the immunological recognition pattern (Western blot) of an anti-cMet reference antibody, DL-21 already characterised in Prat M. et al. J. Cell. Sci. 1998, 111:237-47. The selected antibody (NO-23) was then prepared by growing the hybridoma in Balb/C mice ascites and purified by double precipitation with $NH_4SO_3$ and affinity chromatography on Protein-A sepharose with elution at pH 3.5.

Example 2

Characterisation of the Epitope recognised by the antibody NO-23

The epitope recognised by the monoclonal antibody NO-23 is localized on the β chain of the HGF-R (145 kD), as verified by Western blot after precipitation with a known antibody to demonstrate specificity for HGF-R (DO-24, Upstate Biotechnology Incorporated, Salt Lake City, USA) followed by electrophoretic separation on polyacrylamide gel in SDS, under reducing and non-reducing conditions.

Figure 1:
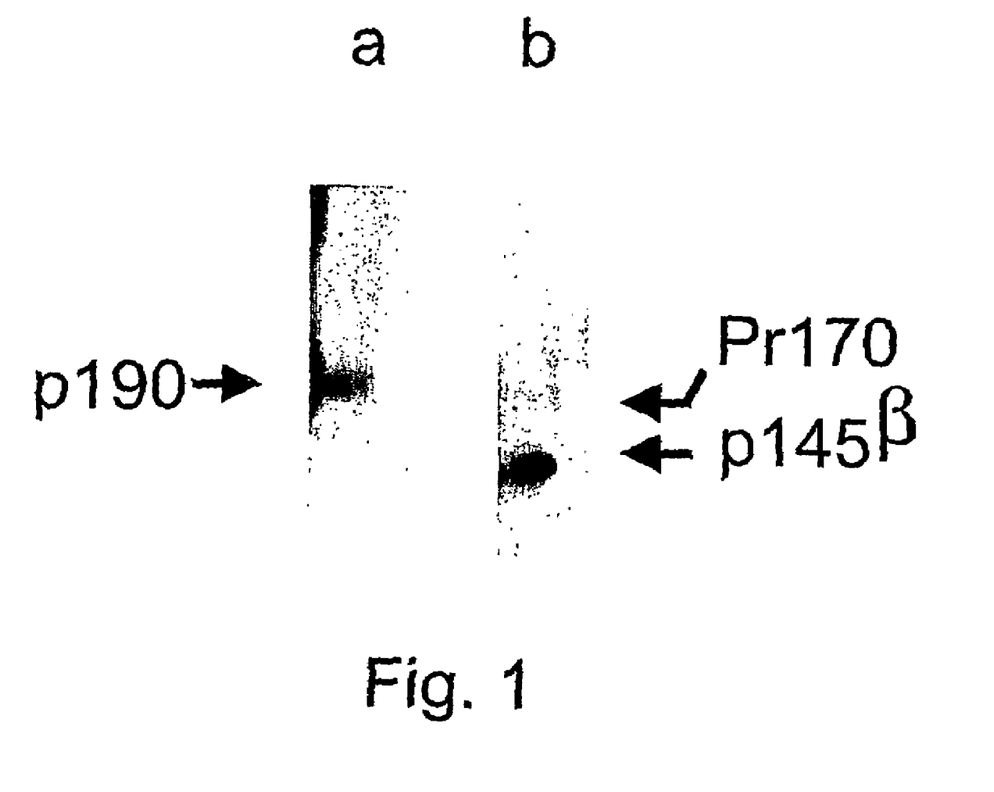
FIG. 1. Mapping by Western blot of the epitope recognized by the antibody of the invention on the HGF-R β chain.

In this respect as FIG. 1 demonstrates under reducing conditions, the antibody NO-23 recognizes two bands with apparent molecular weight 145 kD and 170 kD, corresponding respectively to the β chain and to the precursor of HGF-R, while under non-reducing conditions it recognizes a band of apparent molecular weight 190 kD, corresponding to the heterodimeric HGF-R. The epitope is resistant to denaturation induced by short treatment at 95° C. in Laemmli sample buffer, effected before loading the specimens on SDS-PAGE and is in fact recognized by the antibody even after this electrophoretic separation. Moreover the epitope is resistant to reduction with β-mercaptoethanol (see FIG. 1, lane b), suggesting that it is a linear epitope and does not contain disulphide bridges.

The antibody NO-23 also binds the HGF-R in the presence of non-ionic detergents such as 1% Triton X-100 under the conditions used to select the hybridomas on cell extracts of GTL-1, as described in example 1.

Figure 2:
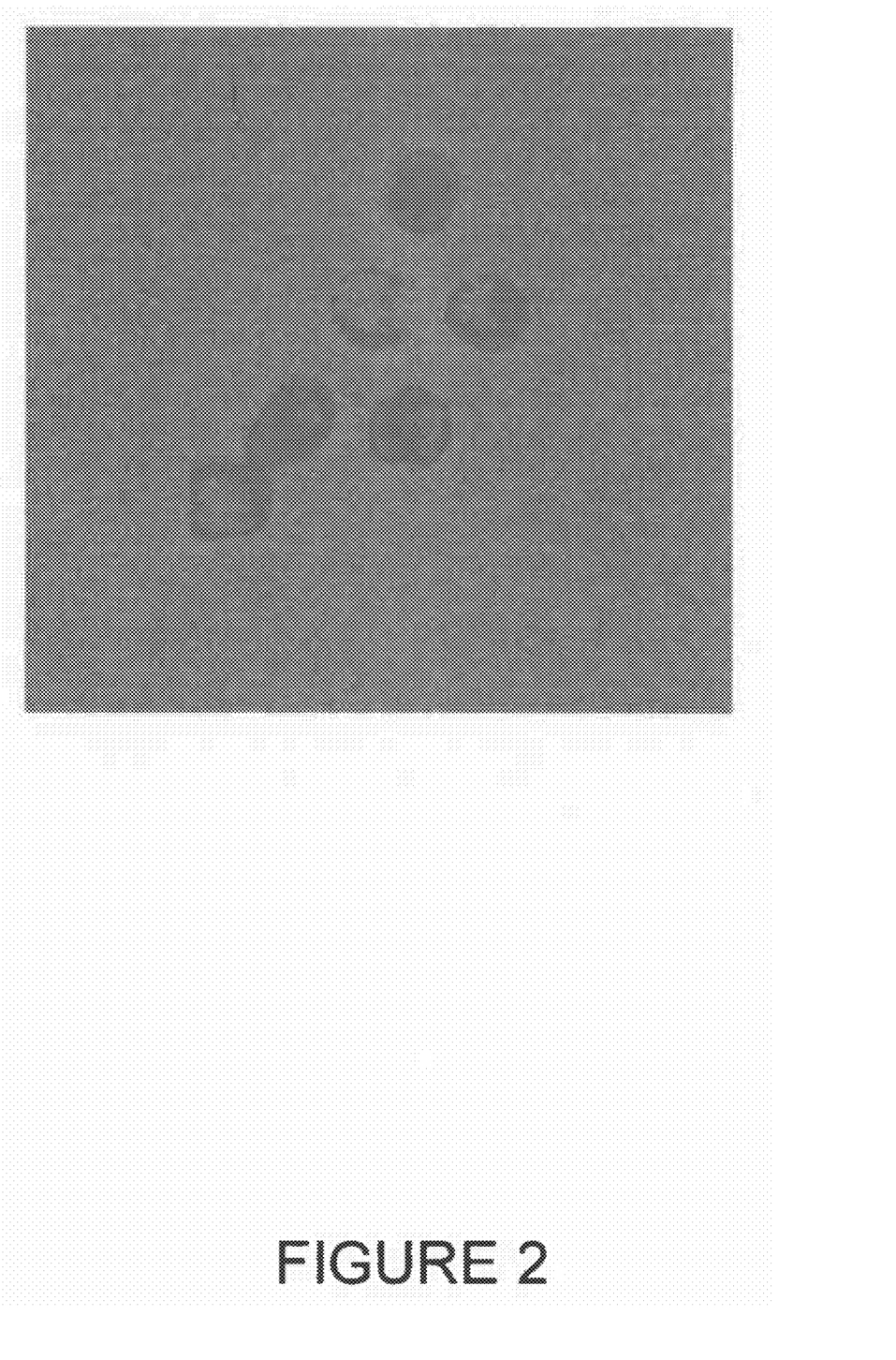
FIG. 2. Immunofluroescence on viable GTL-16 cells.

The antibody recognizes the receptor on cultured GTL-16 cells and consequently the recognized epitope is native and also present on the receptor as expressed on live cells. In the experiment, GTL-16 cells were grown in culture, washed and incubated with the antibody at 4° C., in the presence of sodium azide for 30 min. The antibody binding was visualized by rabbit anti-mouse immunoglobulin antibodies labelled with fluorescein. The immunofluorescence experiment on live GTL-16 cells is shown in FIG. 2: it can be seen that the immunofluorescence is mainly localized at the cell membrane and, as operating under well defined conditions (live cells impermeable to the antibodies and metabolically inactive), it can be concluded that the antibody recognizes an epitope expressed on the extracellular domain of the receptor.

Figure 3:
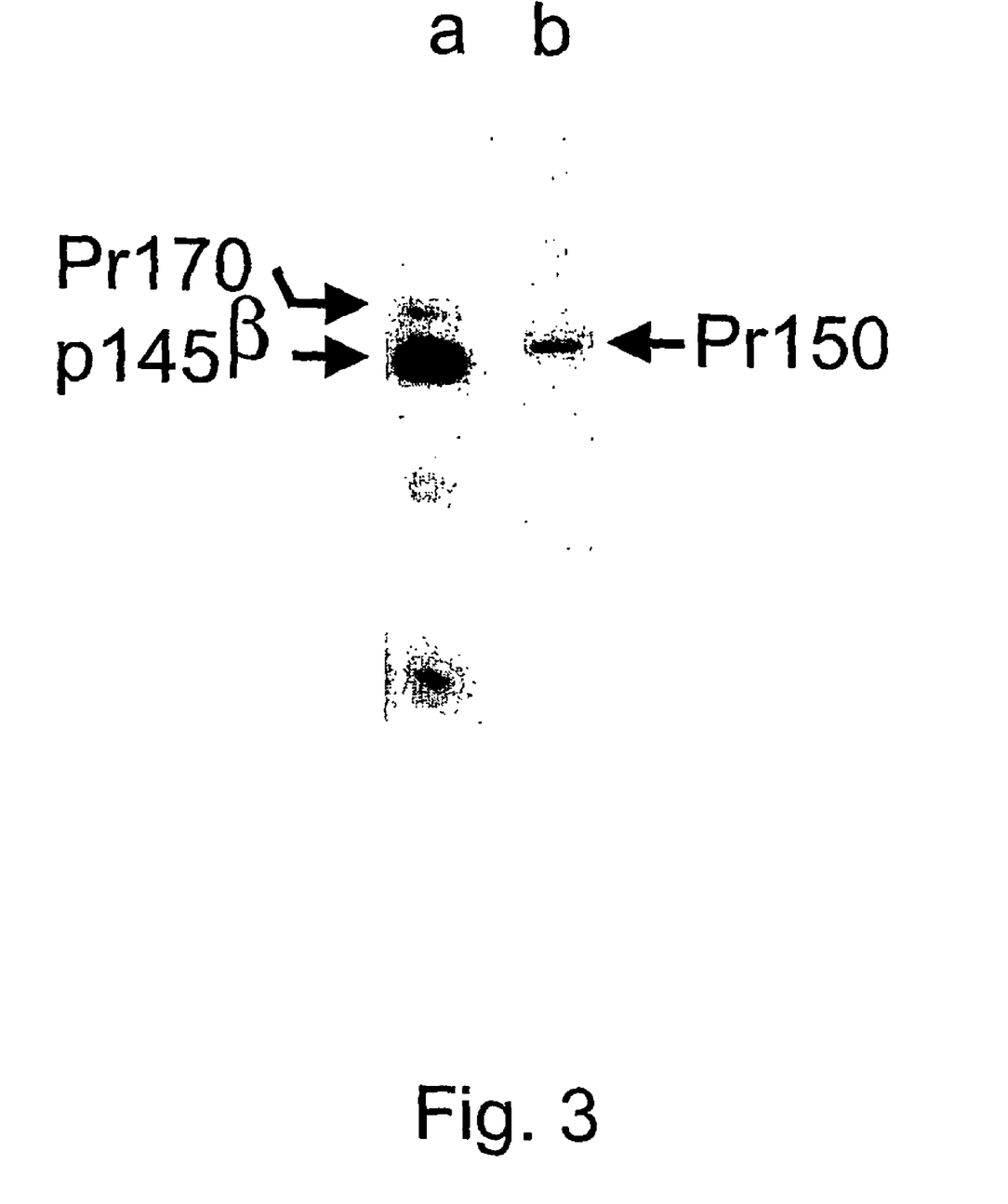
FIG. 3. Immunoprecipitation from extracts of GTL-16 cells grown in the presence of tunicamycin with the antibody of the invention.

The epitope is proteic by nature: GTL-16 cells were labelled with [$^{35}$S] methionine and either treated or not treated with tunicamycin which inhibits N-glycosylation. The cell extracts were then prepared and loaded onto SDS-PAGE under reducing conditions. The experiment shown in FIG. 3 demonstrates that the epitope recognized by the antibody of the invention is present both on the β chain of the glycosylated receptor of cells not treated with tunicamycin and on the 150 kD non-glycosylated precursor in those treated.

Example 3

Structural Characterisation of the Epitope Recognized by the Antibody of the Invention The epitope recognized by the antibody of the invention is different from that recognized both by the natural ligand and by that of other characterised antibodies.

Figure 4:
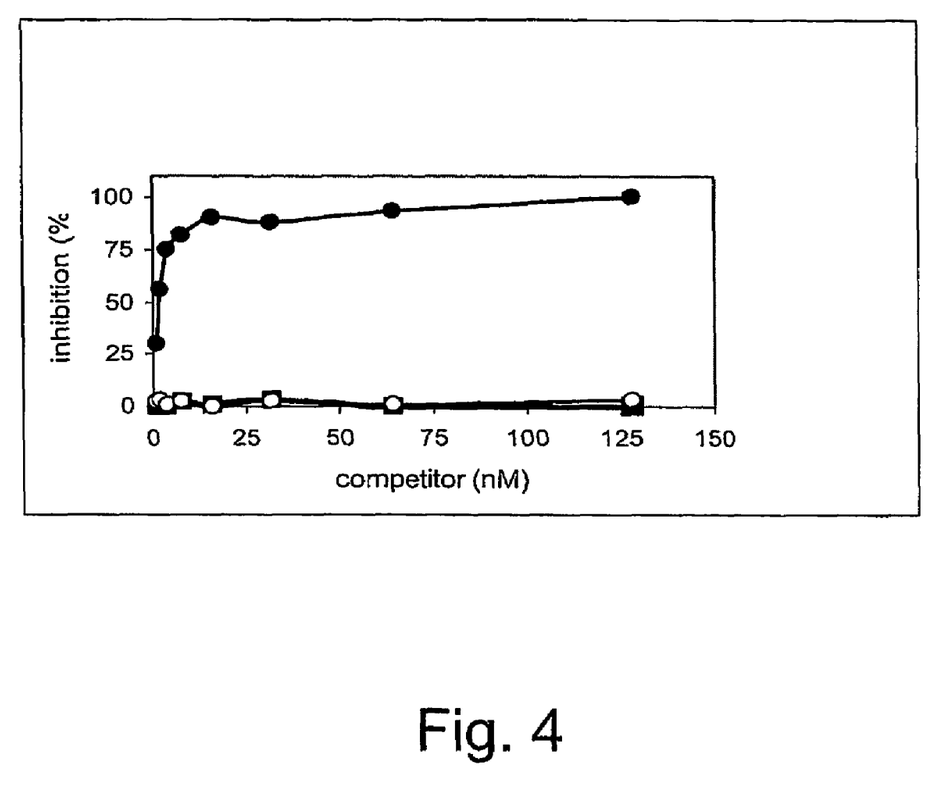
FIG. 4. Double determinant radioimmunometric assay for measuring competition between HGF and monoclonal antibody NO-23 on HGF-R.

FIG. 4 shows the results of experiments conducted by double determinant radioimmunometric assay effected as follows: an antibody already known for its specificity for HGF-R (Mab DL-21, Upstate Biotechnology) was made to adhere to polyvinyl chloride microplates and used to capture the soluble 130 kD HGF-R isoform of the receptor. The binding of $^{125}$I labelled HGR to the soluble receptor adhering to the plate was able to be displaced by the unlabelled HGF, as expected, but not from the antibody of the invention or from a ligand such as Epidermal Growth Factor, used as specificity control. It shows therefore that the antibody NO-23 does not recognize the same HGF-R epitope as recognized by the ligand. In a similar double determinant experiment, in competition with the antibody of the invention labelled with $^{125}$I, antibodies directed against the extracellular domain of HGF-R DO-24 and DL-21 were also used, whether commercially available (Upstate Biotechnology Inc.) or already characterised, such as DN-30 (Prat M, et al. J. Cell Sci., 1998, 111:237-47.1998). The antibody DL-21 was used to coat polyvinyl chloride microplates and to capture the soluble form of the HGF-R receptor. The antibody NO-23 labelled with $^{125}$I was then incubated on the microplates in the presence of the unlabelled anti-HGF-R antibodies which could potentially compete.

Figure 5:
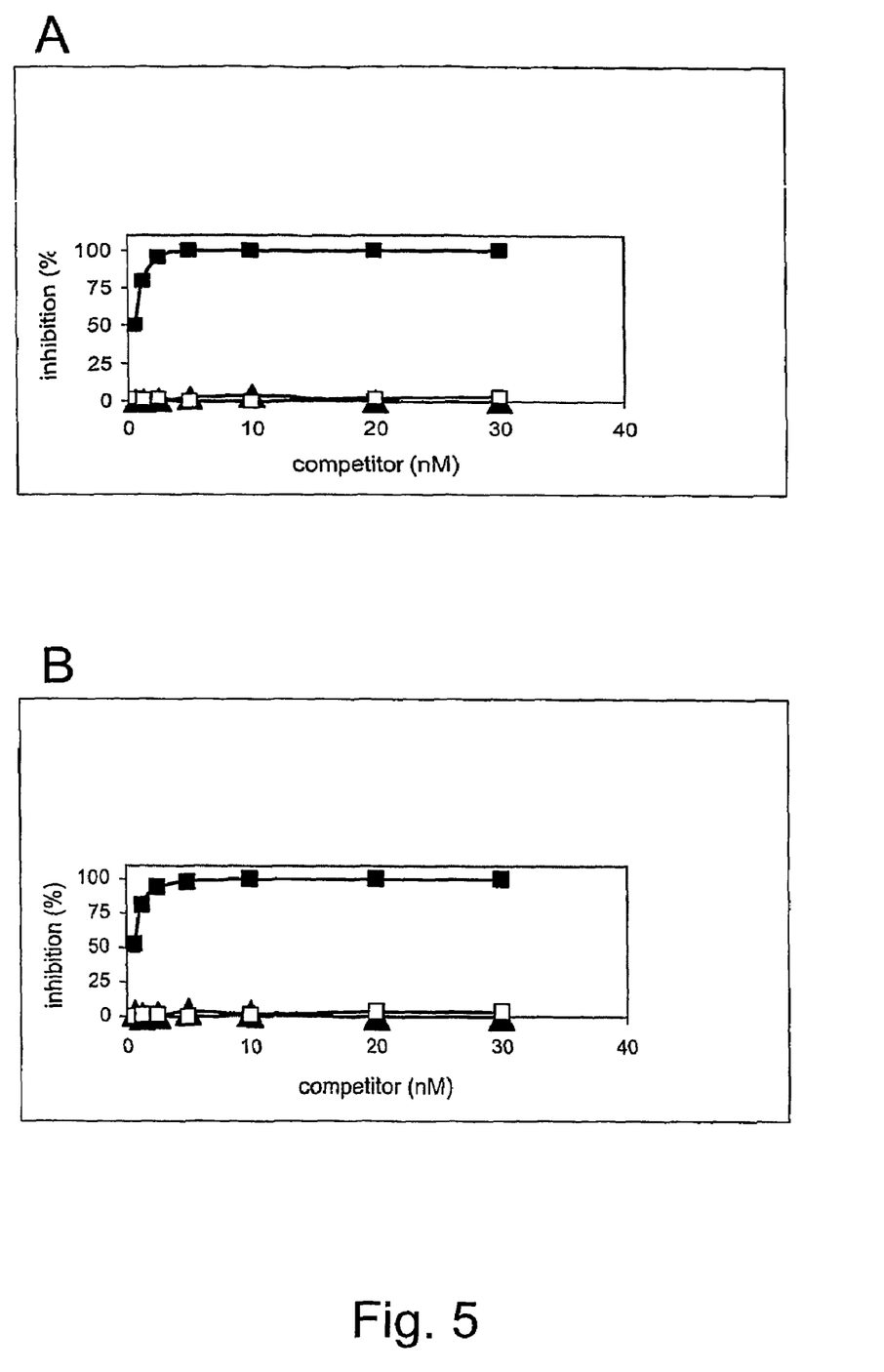
FIG. 5. Double determinant radioimmunometric assay for measuring competition between NO-23 and other known antibodies for the HGF receptor.

Only the actual unlabelled antibody NO-23 was able to compete for binding between $^{125}$I labelled NO-23 and the soluble receptor, as expected. All the other tested antibodies, in particular DO-24 and DN-30 (see FIG. 5A) were unable to compete for binding between NO-23 and the receptor, indicating that the site recognized by the three antibodies on the HGF-R was different. In another experiment the antibody DO-24 was used for capture, and the binding of the antibody of the invention NO-23 radiolabelled at the captured receptor was made to compete with the unlabelled monoclonal antibodies DN-30 and DL-21 and NO-23. Again, in this case, the unlabelled antibody NO-23 was the only one to compete with the radiolabelled antibody NO-23. In FIG. 5, panels A and B summarize the results of the mapping experiments of the HGF-R epitope recognized by NO-23. The data indicate that none of the tested antibodies is able to compete, neither when used for capture, nor in competition in solution, with the antibody of the invention, hence the epitope recognized by NO-23 on the HGF-R is different from that of the other antibodies tested.

Figure 6:
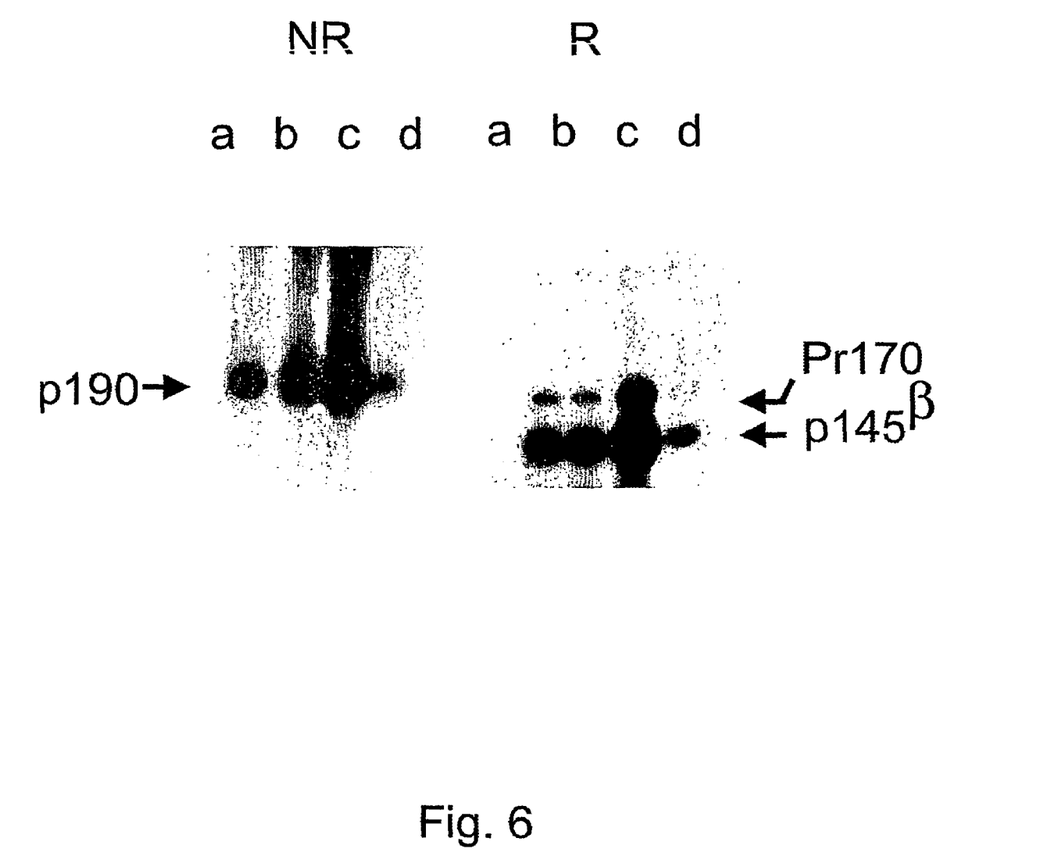

Experiments were also conducted to clarify if the epitope recognized by the antibody NO-23 was an epitope also present on HGF-R receptors of other species, such as rat, mouse and dog. To verify this, extracts of rat H9c2 cells (ATCC cell line # CRL 1446), mouse MLP-29 (Medico E, et al., Mol Biol Cell. 1996, 7:495-504) and dog MDCK (ATCC cell line # CCL-34) and human GTL-16, used as control, were precipitated with the antibody NO-23. The receptor was visualized, after being labelled with radioactive phosphate in a kinase activity assay conducted in the presence of labelled γ-ATP, in all the cell lines used. The result of the experiment is shown in FIG. 6.

Example 4

Functional Characterisation of the Antibody NO-23

Figure 7:
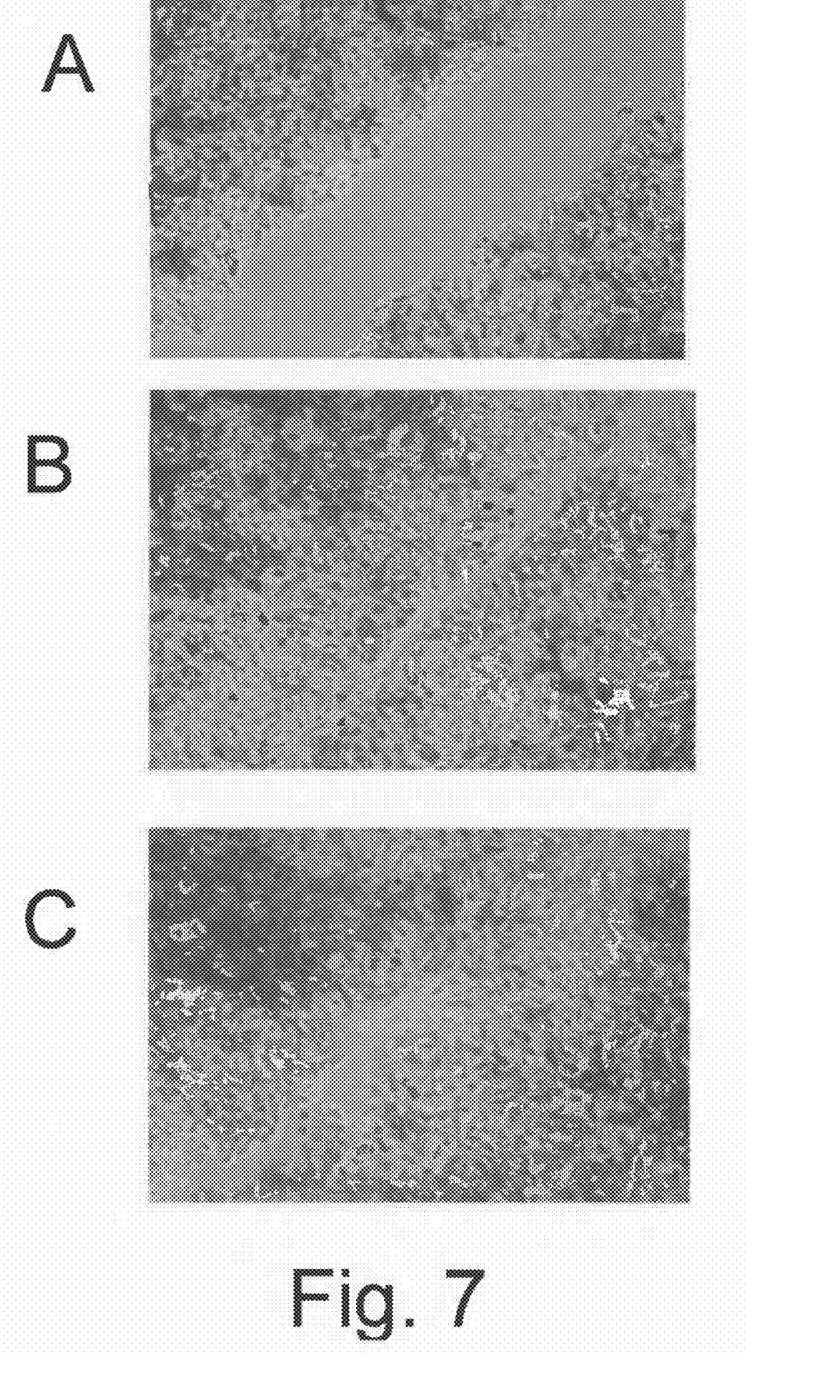
FIG. 7. Healing assay on wound induced in cell monolayer

The agonist activity of the antibody NO-23 was verified by a healing assay on a wound induced on a monolayer of KS-IMM cells (Montaldo et al., 2000). For this purpose, $1.5 \times 10^6$ cells were plated and made to grow in 35 mm wells (Falcon) until confluence. The cells were then incubated in medium containing 0.2% FCS for a further 18 hours. A wound was then produced on the monolayer with a plastic tip, as described in Montaldo et al., J. Cell Physiol., 184: 246-254, 2000. After inducing the wound, the cell monolayer was washed with PBS and incubated for a further 8 hours in medium containing 0.2% FCS alone (FIG. 7, panel A), or with the addition of HGF (1 nM; panel B) or of antibody NO-23 (20 nM; panel C). The cells were then fixed with 11% glutaraldehyde and stained with Crystal Violet in 20% methanol. The photos in FIG. 7 show that following treatment with HGF or with the antibody NO-23, the wound caused on the cell monolayer was almost completely healed compared with the untreated sample and that the antibody therefore has motogenic activity comparable to that of the natural ligand.

Example 5

Figure 10:
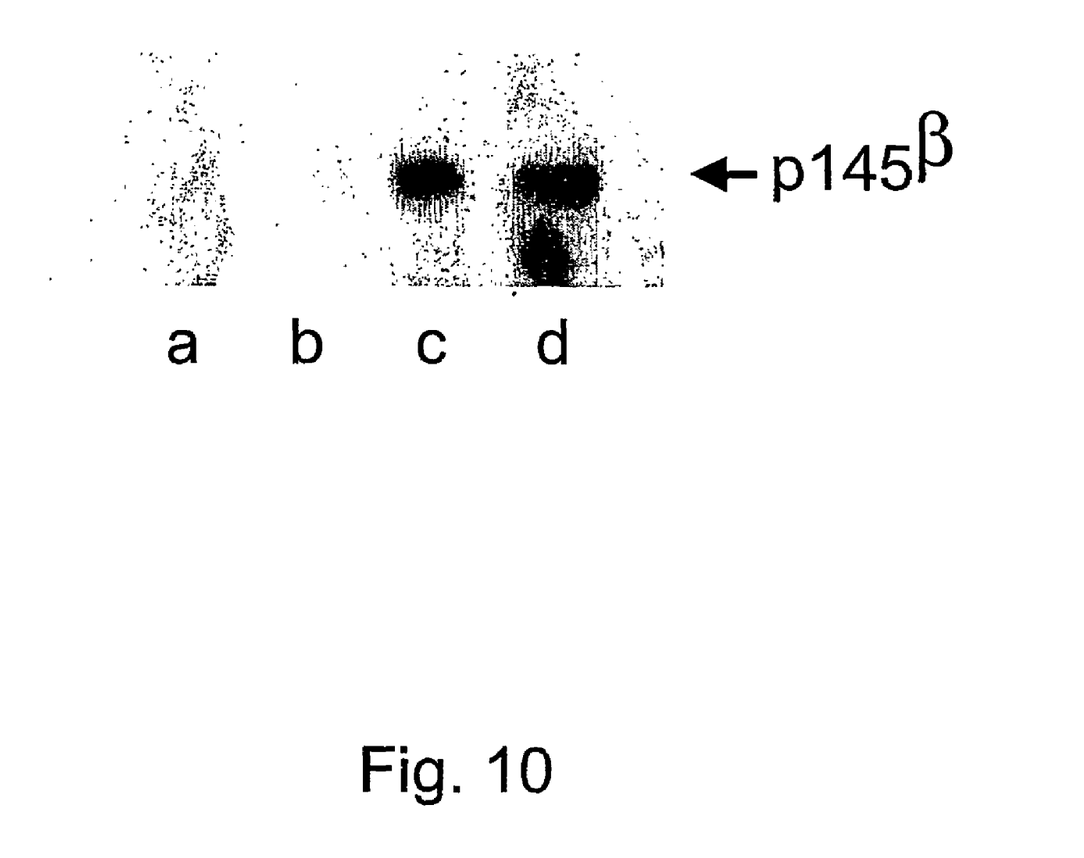
FIG. 10. Detection of HGF-R activation induced by the antibody NO-23 by means of Western Blot.

Induction of HGF-R Phosphorylation by the Antibody NO-23 in Rat Cardiomyocytes Rat H9c2 cardiomyocytes were stimulated with increasing concentrations of antibody NO-23 for 12 minutes at 37° C. (10, 50, 250 nM NO-23, corresponding to lanes b, c, d, FIG. 10) or were untreated (lane a). The cell extracts were then prepared and soluble proteins were precipitated with the antibody DO-24 coated Protein-A Sepharose, separated on SDS-PAGE and transferred to nitrocellulose paper. An anti-phosphotyrosine monoclonal antibody, detected by a goat secondary antibody of anti-mouse immunoglobulin, conjugated with peroxidase, was used for visualizing the phosphorylated form of the receptor following treatment. The assay was determined by means of chemiluminescence (ECL, Amersham). FIG. 10 shows that the antibody NO-23, after binding to the HGF receptor, induces its phosphorylation.

Example 6

Antiapoptotic Effect of the Antibody NO-23

Figure 8:
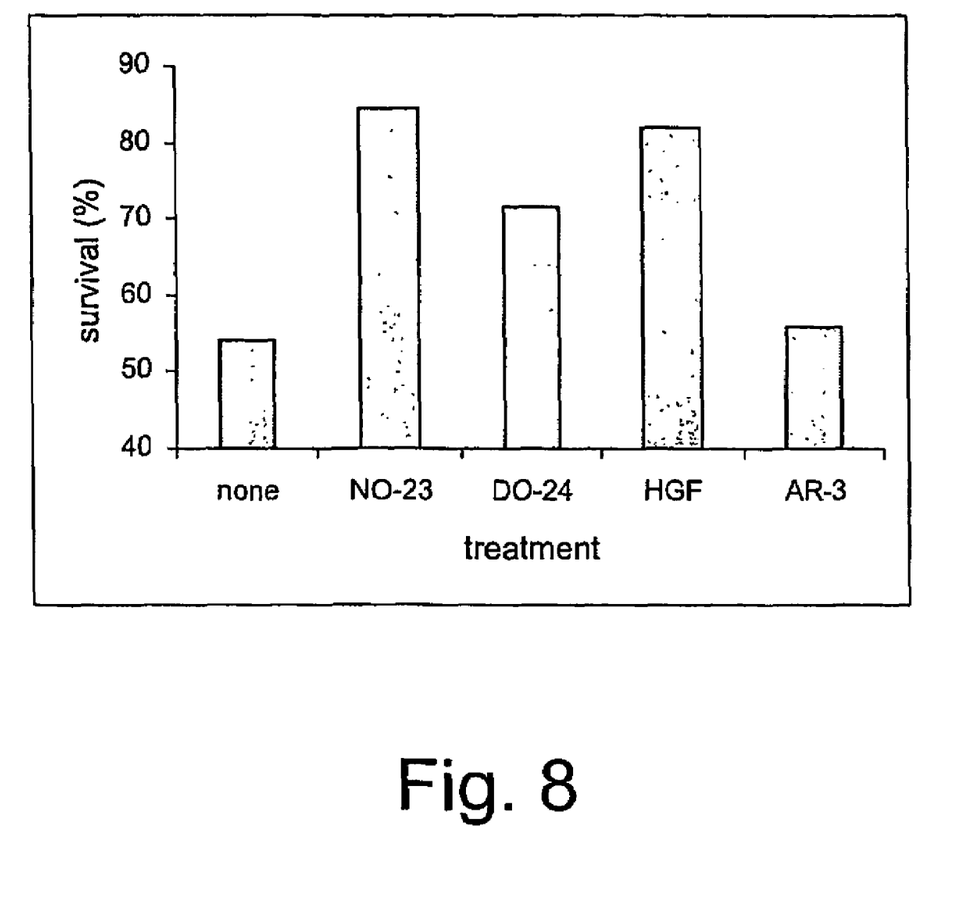
FIG. 8. Protection of rat cardiomyocytes from apoptosis induction by the use of the antibody of the invention NO-23.

Effect on Rat Cardiomyocytes Treated with Daunomycin.
Rat cardiomyocytes (cell line H9c2, catalogue ATCC CRL 1446) were pretreated for 1 hour with the monoclonal antibody of the invention (NO-23), with a reference anti-HGF-R antibody (DO-24), with an uncorrelated antibody (AR-3), with HGF (0.3 nM), or left untreated (none), before inducing apoptosis by treating with the cytotoxic agent daunomycin (10 μM) for 24 hours. The antibodies were used in a final concentration of 20 nM. Under the conditions used for the assay, daunomycin induces apoptosis only in non pre-treated control cells or cells pre-treated with the control antibody AR-3.
Cell survival was evaluated with the calorimetric assay MTT, based on the formation of formazan salts, which are produced only by metabolically active cells and not by cells induced to apoptosis or necrosis. The results of the assay are reported in FIG. 8, where survival in % is defined as (absorbance in each well)/(absorbance in a control well not treated with daunomycin)×100. An antiapoptotic effect greater than that obtained with the natural ligand HGF is observable by pre-treating the cells with the antibody of the invention. In the same assay, the reference anti-HGF-R antibody DO-24 produces a lesser effect than the antibody NO-23, demonstrating the characteristics peculiar to this product.

Figure 9:
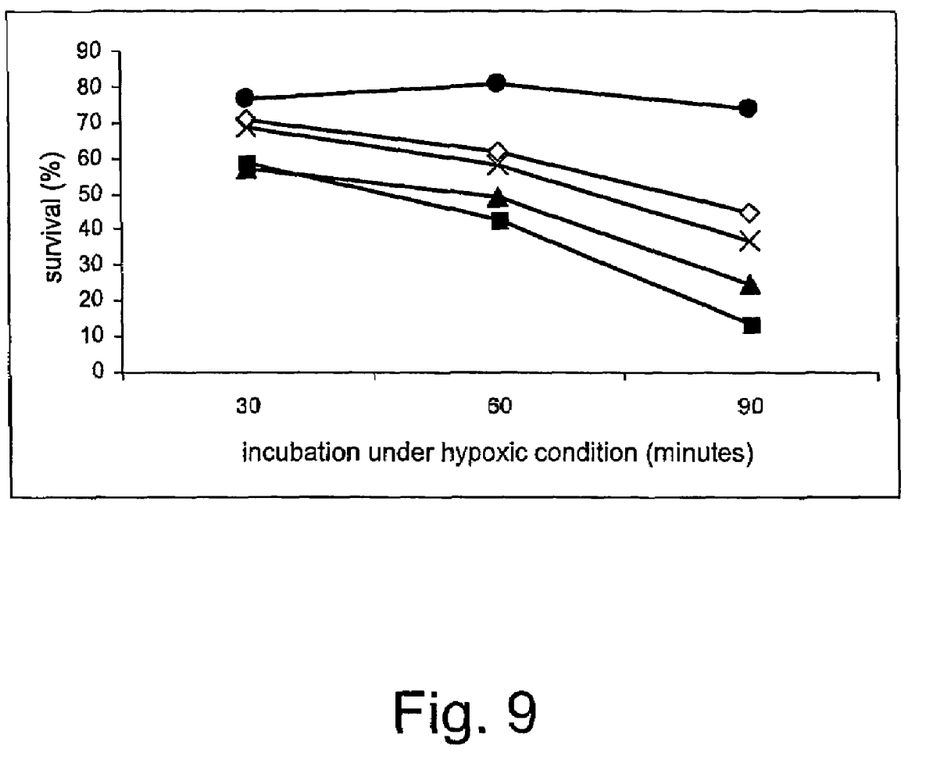
FIG. 9. Protection of primary rat hepatocytes from apoptosis induction by the antibody NO-23.

Effect of the Antibody NO23 on Primary Rat Hepatocytes.
FIG. 9 shows data relating to protection from apoptosis induction obtained by pre-treating primary hepatocytes with the antibody of the invention. Primary hepatocytes were prepared from Wistar strain rats by perfusing the liver with collagenase, as described in Carini et al., 2000, Hepatology, 31: 166-172. They were then resuspended in bicarbonate free buffer and were pre-treated for 15 min. with monoclonal antibody NO-23 at a concentration of 25 or 50 nM, or with an uncorrelated control antibody, AR-3 50 nM, before inducing apoptosis by treatment with 95% $N_2/CO_2$ flow as described in Carini et al., 2000. The control was represented by hepatocytes not treated with the antibody and hepatocytes not treated with the hypoxia treatment. The antibody NO-23 demonstrates a protective effect on primary rat hepatocytes where apoptosis had been induced: in this respect FIG. 9 shows that one hour and a half after treatment under hypoxia conditions, the hepatocytes pre-treated with the antibody NO-23 have a survival rate greater than 60%. Cell survival was measured by counting live cells after staining the non viable hepatocytes with Trypan-Blue.

The invention claimed is:
1. A monoclonal antibody produced by the hybridoma deposited in the Centro di Biotecnologie Avanzate (CBA) ICLC with accession number PD 03001.
2. The antibody of claim 1 in a purified form.
3. A hybridoma cell line deposited in the Centro di Biotecnologie Avanzate (CBA) ICLC with accession number PD 03001.
4. A pharmaceutical composition comprising as the active principle the antibody of claim 1 or fragments thereof which retain the activity of the antibody of claim 1 in combination with suitable excipients and/or diluents.
5. A diagnostic kit comprising the antibody of claim 1 and at least one other anti-hepatocyte growth factor receptor (HGF-R) antibody having specificity different from that of the antibody of claim 1.
6. The diagnostic kit of claim 5 wherein said at least one other anti-HGF-R antibody is against the phosphorylated form of the HGF receptor.
7. The diagnostic kit of claim 5 comprising the antibody of claim 1 in combination with reagents and diluents suitable to perform an immunoassay.
8. A method for inhibiting apoptotic damage to cells comprising contacting said cells with a molecule that specifically binds to the HGF receptor, in an amount sufficient to inhibit apoptosis, wherein the molecule is the antibody of claim 1.
9. The method of claim 8, wherein said cells are selected from the group consisting of hepatocytes, epithelial cells and cardiomyocytes.
10. The antibody of claim 1, wherein said antibody possesses agonist activity to HGF-R.

* * * * *